United States Patent
Pudas et al.

(10) Patent No.: US 11,668,004 B2
(45) Date of Patent: Jun. 6, 2023

(54) SUBSTRATE COATING

(71) Applicant: Picosun Oy, Espoo (FI)

(72) Inventors: Marko Pudas, Espoo (FI); Niku Oksala, Tampere (FI)

(73) Assignee: PICOSUN OY, Espoo (FI)

( * ) Notice: Subject to any disclaimer, the term of this patent is extended or adjusted under 35 U.S.C. 154(b) by 42 days.

(21) Appl. No.: 16/832,286

(22) Filed: Mar. 27, 2020

(65) Prior Publication Data

US 2020/0308695 A1    Oct. 1, 2020

Related U.S. Application Data

(60) Provisional application No. 62/826,430, filed on Mar. 29, 2019.

(51) Int. Cl.
*C23C 16/06* (2006.01)
*C23C 16/00* (2006.01)
*C23C 16/455* (2006.01)

(52) U.S. Cl.
CPC ............ *C23C 16/003* (2013.01); *C23C 16/06* (2013.01); *C23C 16/45525* (2013.01)

(58) Field of Classification Search
CPC .. C23C 16/003; C23C 16/06; C23C 16/45525
See application file for complete search history.

(56) References Cited

U.S. PATENT DOCUMENTS

| 4,609,562 A | * | 9/1986 | Isenberg | C23C 16/455 427/8 |
| 6,086,963 A | * | 7/2000 | Goedicke | C23C 14/54 118/723 VE |
| 6,869,638 B2 | * | 3/2005 | Baum | C23C 16/405 438/785 |
| 7,402,206 B2 | * | 7/2008 | Isberg | C30B 29/52 117/88 |

(Continued)

FOREIGN PATENT DOCUMENTS

| EP | 1728893 A2 | * | 12/2006 | ............ C23C 16/40 |
| JP | 2007-327088 | * | 12/2007 | ............ C23C 14/24 |

(Continued)

OTHER PUBLICATIONS

Vega, J.L., et al., "Study of Gaseous Substrate Fermentations: Carbon Monoxide Conversion to Acetate. 1. Batch Culture". Biotechnology and Bioengineering, vol. 34, pp. 774-784 (1989).*

(Continued)

*Primary Examiner* — Bret P Chen
(74) *Attorney, Agent, or Firm* — Nixon & Vanderhye (57) ABSTRACT

A method for coating a vaporizing substrate includes depositing a film coating 12 on at least a part of a substrate 10 during the time when the substrate undergoes phase transition from essentially liquid phase to gaseous phase, where the substrate includes a chemical substance that participates in chemical deposition reaction(s) in gaseous phase, the gaseous species 101 formed upon vaporizing at least the (Continued)

portion of the substrate material, when undergoing chemical deposition reactions in gaseous phase, produce particulate 11 that forms at least one coating layer to produce the film coating 12.

19 Claims, 2 Drawing Sheets

(56) References Cited

U.S. PATENT DOCUMENTS

| | | | | |
|---|---|---|---|---|
| 8,178,330 | B2* | 5/2012 | Trevethick | C12M 29/04 435/161 |
| 8,211,235 | B2 | 7/2012 | Lindfors | |
| 8,685,293 | B1* | 4/2014 | Coppa | B23K 26/40 264/5 |
| 2002/0176097 | A1* | 11/2002 | Rodgers | H01L 21/6715 356/630 |
| 2005/0042376 | A1* | 2/2005 | Xin | C23C 14/548 427/255.32 |
| 2008/0282733 | A1* | 11/2008 | Tolwani | C12P 5/023 63/32 |
| 2010/0098904 | A1* | 4/2010 | Dai | B82Y 40/00 428/119 |
| 2011/0151135 | A1* | 6/2011 | Nagae | C23C 14/221 427/523 |
| 2013/0011318 | A1* | 1/2013 | Nakatani | C04B 35/62259 423/325 |
| 2013/0011804 | A1* | 1/2013 | Seo | C23C 14/543 432/13 |
| 2014/0144323 | A1* | 5/2014 | Chen | B01D 53/228 96/12 |
| 2014/0367257 | A1* | 12/2014 | Nogami | G01N 1/4005 204/403.06 |
| 2015/0250731 | A1 | 9/2015 | Hoppu | |
| 2016/0237398 | A1* | 8/2016 | Kalyuzhnaya | C12N 1/20 |
| 2018/0154019 | A1* | 6/2018 | Voelcker | A61P 17/02 |
| 2018/0296494 | A1* | 10/2018 | Shalev | A61L 27/54 |
| 2019/0067580 | A1* | 2/2019 | Nishida | C23C 14/24 |

FOREIGN PATENT DOCUMENTS

| | | | | |
|---|---|---|---|---|
| JP | 2011-82196 | * | 4/2011 | H01L 21/31 |
| WO | WO 2007/093401 A2 | * | 8/2007 | C09C 1/62 |
| WO | WO 2011/131825 A1 | * | 10/2011 | C23C 16/448 |
| WO | WO 2012/080458 A1 | * | 6/2012 | B23K 26/00 |

OTHER PUBLICATIONS

Beverly, III, R.E., et al., "Channel spreading and substrate vaporization in surface-spark discharges". Journal of Applied Physics 48, 3609 (1977), 1 page. Abstract Only.*

Beverly III, R.E., "Channel spreading and substrate vaporization in surfacespark discharges". Journal of Applied Physics 48, 3609-3611 (1977).*

Patankar, Neelesh A., "Vapor Stabilizing Substrates for Superhydrophobicity and Superslip". Langmuir, 2010, 26(11), 8783-8786.*

Beverly III, R.E., "Channel spreading and substrate vaporization in surface spark discharges". Journal of Applied Physics, vol. 48, No. 8, Aug. 1977, pp. 3609-3611.*

Hu, Jun, et al., "Hydride vapor phase epitaxy for gallium nitride substrate". Journal of Semiconductors (2019) 40, 101801, pp. 1-10.*

Kang, Minsoo, et al., "Evaluation of Particle Bounce in Various Collection Substrates to be Used as Vaporizer in Aerosol Mass Spectrometer". Aerosol Science and Technology, 49:5 (2015) 332-339.*

Extended European Search Report issued in European Patent Application No. 20165547.9 dated Jul. 28, 2020.

Boehler, C. et al., "A Simple Approach for Molecular Controlled Release based on Atomic Layer Deposition Hybridized Organic-Inorganic Layers," Scientific Reports, vol. 6, No. 1, Jan. 21, 2016.

Perrotta, A. et al., "Strategies for Drug Encapsulation and Controlled Delivery Based on Vapor-Phase Deposited Thin Films," Advanced Engineering Materials, vol. 20, No. 3, Sep. 19, 2017.

* cited by examiner

Figure 1

Figure 2

SUBSTRATE COATING

FIELD OF THE INVENTION

The present invention generally relates to substrate processing methods and apparatus. In particular, the invention pertains to a process for coating vaporizing media by chemical deposition methods.

BACKGROUND OF THE INVENTION

Chemical deposition methods occurring in vapour phase, such as Chemical Vapor Deposition (CVD) and Atomic Layer Deposition (ALD), are extensively described in the art. ALD technology generally regarded as a subclass of CVD processes has proved an efficient tool for manufacturing high-quality conformal coatings on various substrates.

ALD is based on alternating self-saturative surface reactions, wherein different reactants (precursors) provided as chemical compounds or elements in a nonreactive (inert) gaseous carrier are sequentially pulsed into a reaction space accommodating a substrate. Deposition of a reactant is followed by purging the substrate by inert gas. Conventional ALD cycle proceeds in two half-reactions (pulse first precursor—purge; pulse second precursor—purge), whereby a layer of material is formed in a self-limiting (self-saturating) manner, typically being 0,05—0,2 nm thick. The cycle is repeated as many times as required for obtaining a film with a predetermined thickness. Typical substrate exposure time for each precursor ranges within 0,01-1 seconds.

The vapour-phase coating processes, such as CVD and ALD thus rely on delivery of a reactant towards a sample (the substrate) in gaseous phase. In surface coating processes, the reactions typically occur only on the sample surface, whereas reactions in the gas phase are avoided. Thus, if reactive (precursor) gasses, such as trimethylaluminium (TMA) and $H_2O$ (common ALD reactants to produce aluminium oxide $Al_xO_y$, such as $Al_2O_3$) react in gas phase, they generate particles, which will eventually grow to the sizes within a range of micrometers.

ALD technique typically requires that only one precursor substance (a reactant) is present in gas phase at once, due to the fact that ALD reactions are sequential and separated in time. If both precursor substances/gasses are simultaneously present in gas phase, the process generates particles, which is not desired and in most instances even detrimental for ALD processes.

On the opposite, the processes aiming at particle generation, such as production of nano-powders, typically involve the reactions between substances in the gas phase.

At present, use of colloid substances, such as hydrogels, is common in biomedical applications. In some areas, such as in preparation of medicines and sustained-release drug delivery, colloids, such as hydrogel, require deposition of thin coatings on their surfaces. However, in conditions of chemical deposition in the vapour phase, such as ALD conditions, hydrogel materials evaporate.

In this regard, an update in the field of vapour-deposition based methods, such as atomic layer deposition technology, is still desired, in view of addressing challenges associated with the application of said methods in producing coated items from the substrates comprising or consisting of material evaporating in conditions of conventional vapour-phase deposition processes.

SUMMARY

An objective of the present invention is to solve or to at least alleviate each of the problems arising from the limitations and disadvantages of the related art. The objective is achieved by various embodiments of a method and device for coating a vaporizing substrate, a coated substrate and related uses. In an aspect, a method for coating a vaporizing substrate is provided according to what is defined in independent claim 1.

In embodiment, a method for coating a vaporizing substrate is provided, in which method a film coating comprising at least one coating layer is deposited on at least a portion of a substrate material that undergoes phase transition from essentially liquid phase to gaseous phase, and wherein the substrate comprises a chemical substance that participates in chemical deposition reaction(s) in gaseous phase.

In embodiment, the film coating is deposited onto the substrate material being vaporized from at least a surface of the substrate.

In embodiment, the method comprises formation of gaseous species upon vaporizing at least the portion of the substrate material, wherein said gaseous species, when undergoing chemical deposition reactions in gaseous phase, produce particulate that forms at least one coating layer on at least part of the surface of the substrate.

The at least one coating layer can comprise a metal compound.

In embodiment, at least density and/or porosity of the film coating gradually change(s) in vertical direction.

In embodiment, the vaporizing substrate is an essentially liquid substrate. In embodiment, the vaporizing substrate is a colloid substrate, such as gel, hydrogel or sol-gel.

In embodiment, the vaporizing substrate undergoes chemical reactions according to the principles of chemical deposition in vapour phase, such as Chemical Vapour Deposition (CVD) or Atomic Layer Deposition (ALD).

In embodiment, the method comprises formation of the particulate, when the gaseous species formed upon vaporizing of at least the portion of the substrate material undergo chemical deposition reaction(s) with a chemical precursor or precursors, such as ALD precursor(s).

In embodiment, the substrate comprises a biodegradable material. In embodiment, the substrate comprises a bioactive compound, a pharmaceutically active compound, or a combination thereof. In some configurations, the substrate comprises at least one of bioactive compound, optionally configured as a pharmaceutically active compound.

In embodiment, the method further comprises formation, by chemical deposition, of at least one additional coat over the surface of the substrate already coated with the film coating to provide conformal encapsulation thereof. The additional coat can be deposited by a process of chemical deposition in vapour phase, such as Chemical Vapour Deposition or Atomic Layer Deposition Alternatively, the vaporizing substrate material may produce particulate suspended in gaseous phase, which particulate undergoes chemical deposition reaction(s) in gaseous phase, whereby particles deposited with an at least one coating layer are produced. In such a manner, a coated particulate substrate can be produced.

In an aspect, a method for producing of at least partially encapsulated substrate is provided according to what is defined in independent claim 9.

In another aspect, a product is provided, according to what is defined in the independent claim 13.

In embodiment, the product comprises a substrate and a film coating deposited on at least a portion of the substrate, said film coating comprising at least one coating layer, wherein at least density and/or porosity of the film coating gradually change(s) in vertical direction and wherein the substrate is an essentially liquid substrate or a colloid substrate, such as gel, hydrogel or sol-gel. The product can further comprise an additional coat formed over the surface of the substrate already coated with the film coating, to provide conformal encapsulation thereof.

The product is thus provided as at least partially encapsulated substrate provided in the form of any one of liquid, gel, hydrogel or sol-gel.

The invention further concerns a composition for gradual release. The composition comprises or consist of the product according to the embodiments, and it is provided in the form of a bioactive composition or a pharmaceutical preparation.

In further aspect, a device for coating a vaporizing substrate is further provided, according to what is defined in independent claim 14.

In embodiment, the device is configured to deposit a film coating comprising at least one coating layer on at least a portion of a substrate material that undergoes phase transition from essentially liquid phase to gaseous phase, wherein said substrate comprises a chemical substance that participates in chemical deposition reaction(s) in gaseous phase.

In embodiment, the device is configured as any one of a Chemical Vapour Deposition reactor, an Atomic Layer Deposition reactor, and a Plasma-Enhanced Atomic Layer Deposition reactor.

It is an object of certain embodiments of the invention to generate powder on the surface of the substrate to be coated; to further generate continuous conformal coating on top of the said powder, wherein the coated material is bio-degradable and/or soluble in aqueous solutions.

In an embodiment, the coating comprises a metal compound and it is deposited with atomic layer deposition (ALD).

Different non-binding example aspects and embodiments have been presented in the foregoing. The above embodiments and embodiments described later in this description are used to explain selected aspects or steps that may be utilized in implementations of the present invention. It should be appreciated that corresponding embodiments apply to other example aspects as well. Any appropriate combinations of the embodiments can be formed.

Without limiting the scope and interpretation of the patent claims, certain technical effects of one or more of the example embodiments disclosed herein are listed in the following.

Pharmaceutical agents, depending on the route of administration (oral, mucosal, via respiratory tract, intravenous, subcutaneous, intramuscular, intrathecal or directly infused into organ parenchyme or arterial blood supply) can be coated by the method(s) disclosed hereby to regulate their release, to phase the release or to modify their pharmacokinetics in any other way. Some applications may require long-term effect (depot) which requires controlled, slow (extended in time) release of the pharmaceutical agents. Some applications may require different kinetics in different phases, i.e. in a way that the rate of release changes over time. Other applications may require release of different compounds in a controlled fashion, modifying both the rate of release and/or the compound released. Means to coat the medicine (the coating) also enables a pharmaceutical agent administered orally to be modulated in such a way that it tolerates harsh conditions in the stomach, in which the agent is exposed to gastric acid, and on the other hand, the alkali conditions at the beginning of the intestinal tract. In such a way, bioavailability may be enhanced in order to minimize the amount of pharmaceutical agent and local side effects and to maximize biological/pharmaceutical effect exerted by the compound. The invention also allowing for increasing/improving patient compliance by reducing the number of times the drug must be taken. Other applications that benefit from the obtained performance of releasing the embedded material from the substrate, e.g. a gel-like substrate, are biocides, which need to be released with controlled dosage over time in the operating (use) environment.

In the present disclosure, materials with a layer thickness below 1 micrometer (μm) are referred to as "thin films".

In the present disclosure, the term "gel" is generally utilized to indicate an essentially solid or semi-solid form of colloid provided in generally more solid form than a sol (colloid solution in essentially liquid state). The term "hydrogel" refers to a gel in which the liquid component is water. The term "sol-gel" is indicative of a colloid capable of alternating between sol and gel states.

In the present disclosure, the terms "vaporizing" and "evaporating" are used interchangeably.

In the context of present disclosure, the terms "particle" and "particulate" are used to designate a self-standing entity and a plurality of such entities, accordingly, formed upon deposition reaction involving phase transition from an essentially gaseous phase to a solid phase through a process of gas-phase (vapour-phase) deposition.

The expression "a number of" refers herein to any positive integer starting from one (1), e.g. to one, two, or three; whereas the expression "a plurality of" refers herein to any positive integer starting from two (2), e.g. to two, three, or four.

The terms "first" and "second" are not intended to denote any order, quantity, or importance, but rather are used to merely distinguish one element from another.

FIELD OF THE INVENTION

The present invention generally relates to substrate processing methods and apparatus. In particular, the invention pertains to a process for coating vaporizing media by chemical deposition methods.

BRIEF DESCRIPTION OF THE DRAWINGS

The invention will now be described, by way of example only, with reference to the accompanying drawings, in which:

FIG. 1 shows a method for coating vaporizing substrate and for producing an encapsulated substrate, according to the embodiments;

FIG. 2 shows a method for producing encapsulated substrate, wherein the substrate is a medicine (a pharmaceutical preparation).

DETAILED DESCRIPTION

The invention, according to one aspect, pertains to a method for coating a vaporizing substrate. In the present context, the expression "vaporizing substrate" refers to the substrate being vaporized. Coating thus occurs during the process of vaporization of said substrate. In the method, a film coating 12 is deposited on at least a portion of a substrate material 10 that undergoes phase transition from essentially liquid phase to gaseous phase (vapour phase), and wherein the substrate comprises a chemical substance that enters- and participates in chemical deposition reaction(s) in gaseous phase (vapour phase).

The film coating comprises at least one coating layer 121, 122. The coating layers 121, 122 are further referred to as sublayers.

To avoid confusion, in present disclosure, the terms "gaseous phase" and "gas phase" are used to designate the state of matter of a substance, e.g. vapour. The term "vapour" is used with reference to a gaseous phase (gas phase) of typically a non-gaseous substrate, viz. the substrate that under the normal conditions exists in a non-gaseous state, wherein said substrate, upon vaporizing, diffuses into the ambient provided as a gaseous phase (e.g. air or other gas). Normal conditions should be generally understood as environmental conditions established at room temperature (about 20° C.) and atmospheric pressure (about 1 atm or 101 kPa).

Figure 1:
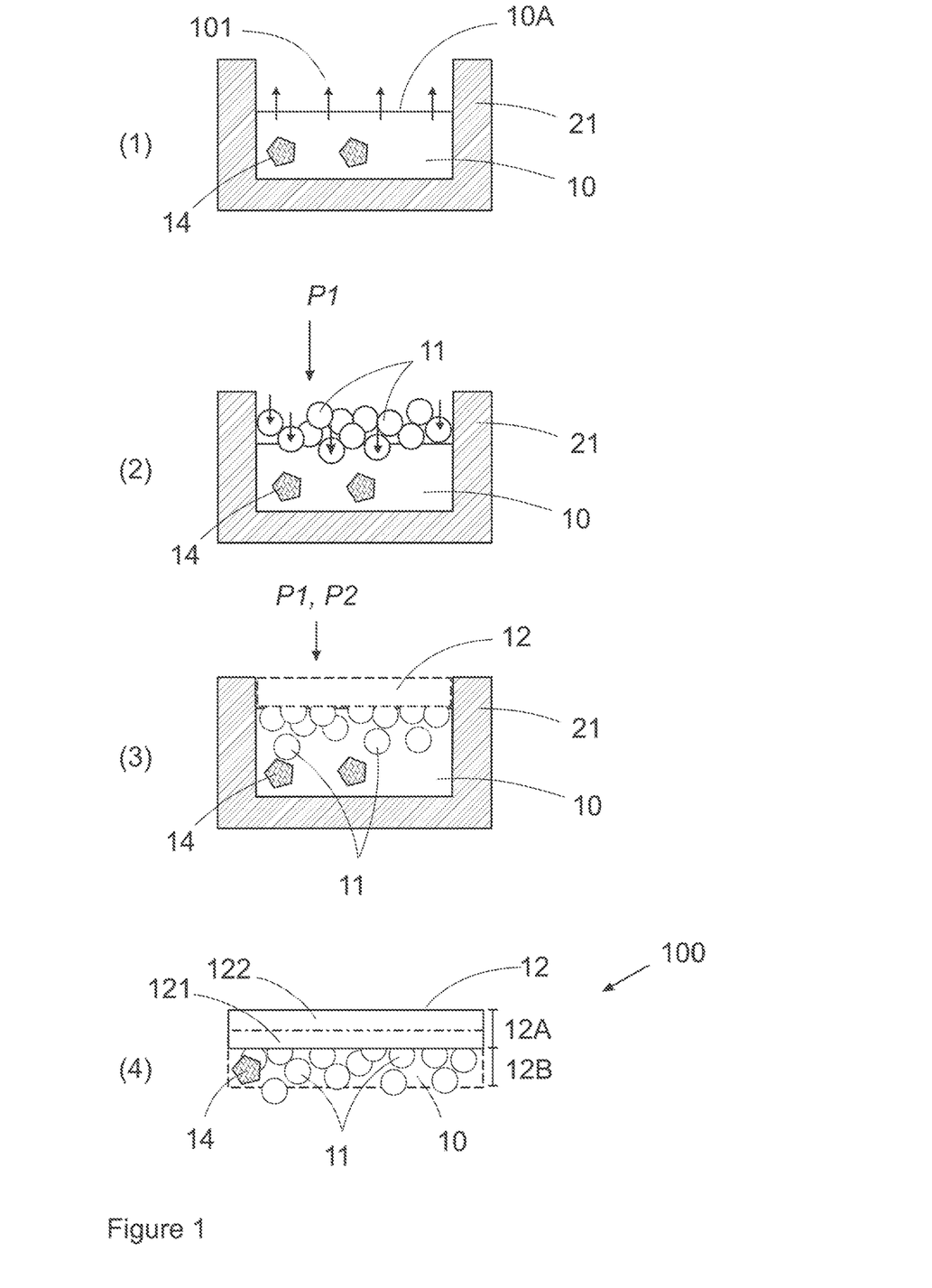

FIG. 1 is illustrative of an exemplary embodiment of the method. The method starts at (1) (FIG. 1), by vaporizing at least a portion of the substrate material 10 disposed in an exemplary substrate holder 21. Vaporization is preferably carried out in a closed/sealed reaction chamber (not shown) of an exemplary device for coating a vaporizing substrate (described herein below) in conditions of elevated temperature (in the chamber), such as within a range of about 30° C. to about 350 ° C., for example. However, with certain reactive- and low boiling point chemicals, the temperature can be reduced to below 30° C., such as within a range of about 0 ° C. to about 30° C. The reaction chamber is preferably kept under vacuum (pressure maintained at a level of about 100 Pa (1 mbar) or preferably less). In some instances, pressure in the reaction chamber is set-up up to the same level as the atmospheric pressure.

In some instances, the temperature of the substrate 10 can be maintained sub-zero.

The substrate holder 21 is shown on FIG. 1 as a receptacle (e.g. a cup), however, the substrate holder can be provided as an item having an essentially flat surface (e.g. a plate) optionally having a number of protrusions (e.g. pins or studs) for holding the substrate. At least the portion of the substrate 10 being vaporized is shown by arrows (1, FIG. 1). At least one substrate holder 21 is placed into the reaction chamber that forms a reaction space (not shown).

Vaporization process typically starts at the surface 10A of the substrate.

At least a portion of the substrate material 10, upon being vaporized, produces gaseous species 101 (also indicated by arrows, 1, FIG. 1).

The substrate 10 can be provided, prior to vaporizing, as an essentially liquid substrate (e.g. water, any aqueous or non-aqueous solution). Alternatively, the substrate can be provided, prior to vaporizing, as a colloid substance, such as gel, hydrogel or sol-gel. Any other type of essentially colloid(al) matter and colloid systems, such as emulsions, for example, are not excluded. Colloid systems, such as gel, for example, are two-phase systems consisting of a solid medium and a liquid phase. Liquid contained in such substrate vaporizes/evaporates to from the gaseous phase to produce gaseous species 101.

The gaseous species 101 can be defined as any one of the atoms, molecules, molecular clusters, ions, and free radicals produced upon vaporization and diffused/suspended in gaseous phase. The terms "diffuse(d)" and "suspend(ed)" are used hereby to merely indicate the fact that the particles of matter released from the substrate (essentially liquid phase) into the gaseous phase "float" in said gaseous phase, when not held by intermolecular bonds.

Thus, in exemplary configuration, the substrate 10 (provided as any one of liquid or colloid) undergoes vaporization, whereby water vaporizes from the surface 10A of said substrate and water molecules become released into the gaseous phase as the gaseous species 101. In practice, vaporizing gaseous species flow into the ambient created in the reaction space.

The gaseous species 101 react, in gaseous phase, with a precursor P1 (2, FIG. 1), directed into the reaction chamber, via a feedline, during a predetermined period of time (pulse). The precursor is a chemical compound reactive with the gaseous species 101.

The gaseous species 101, when undergoing chemical deposition reactions in gaseous phase, produce particulate 11 that forms at least one coating layer on at least part of the surface of the substrate. The particulate 11 is provided as a plurality of essentially solid particles having size within a range of about 0,2 nm-1 mm. In some instances, the particulate 11 is referred to as a powder.

By way of example, a reaction between water (the species 101) and the TMA (precursor chemical P1) can be conducted. Reaction between these compounds produces aluminium oxide (e.g. $Al_2O_3$), in the form of particulate 11 (2, FIG. 1). The particulate 11 deposits, from the gaseous phase, onto the substrate 10 to form a coating layer (e.g. about 1 angstrom layer). Formation of the coating layer is illustrated on FIG. 1, step 2, by bubbles that deposit ("fall down", see arrows) onto the substrate 10. Any combination of (co) reactants can be utilized.

The method continues at 3 (FIG. 1), with optionally directing a second precursor P2, different from a first precursor P1, into the reaction space. Additionally or alternatively, a first precursor P1 can be again pulsed into the reaction space. During each pulse, a coating (sub)layer is deposited on the substrate, as described above. In practice, the coating layers are "stacked" on the top of one another) to form the film coating 12 (3, FIG. 1). Deposition of the coating layer(s) and of the coating film can be implemented by any one of the CVD or ALD methods.

In predetermined conditions created in the reaction space, the gaseous species 101 continue vaporizing through the deposited coating layers until the depth/thickness of the "stack" reaches approximately 10 nm to 100 nm. Thereafter, the precursor flow may be adjusted such, as to react with a (top) surface of the stack (not shown).

In some embodiments, the precursors are pulsed into the reaction space one at a time. Overall, any amount of different precursors may be utilized for the entire process, e.g. P1, P2, P3 etc.

By "stacking" the coating layers on the top of one another, the film coating 12 is thus formed on the surface of the substrate (3, FIG. 1). The film coating 12 has depth/thickness within a range of about 10 nm-2 mm. Upon vaporizing the substrate 10 (accompanied by generation of gaseous species 101) and depositing the particulate layer-wise onto said substrate, the unreacted substrate material 10 is diminished, which process is proportional to growth of the film 12 on the surface of the substrate 10 (see 4, FIG. 1).

The coating layers provided as the sublayers of the coating film 12 are schematically indicated at step 4, FIG. 1, by reference numerals 121, 122.

After the film 12 of desired thickness is deposited onto the substrate, the substrate holder 21 can be removed (4, FIG. 1). At step 4, a product 100 is thus generated comprising the substrate 10 at least partially coated/encapsulated with the film coating 12 comprising at least one coating layer 121, 122.

At least density and/or porosity of said film coating 12 gradually change(s) in vertical direction. By vertical direction we refer hereby to a direction along a cross-section between the (unreacted) substrate 10 and the topmost layer of the coating film 12. The gradient can be at least partially adjusted by varying the ratio of chemicals P1 and P2. In a configuration shown on FIG. 1 the film 12 has a denser layer on the top (indicated as 12A) and a more porous, amorphous layer (indicated as 12B) underneath. To emphasize gradual transition, in terms of at least density and/or porosity, between the topmost coating 12 and the unreacted substrate 10 (4, FIG. 1), the more dense layer 12A is indicated to further comprise sublayers 121, 122 with variable density and/or porosity. It should be understood that FIG. 1 serves explanative purpose only and the number of coating (sub) layers 121, 122 may vary to establish a gradient generally designated as 12A-12B within the film coating 12.

At step 4, a particulate substrate 100 is produced, which comprises particles of matter coated with the coating film 12 comprising at least one coating layer.

Thickness of the film coating 12 and its sublayers 121, 122, accordingly, is adjustable by regulating the deposition reaction conditions.

The precursor(s) can comprise or consist of metal compound(s). In some configurations, the at least one coating layer 121, 122 can comprise at least one metal compound.

In the method, the vaporizing substrate 10 preferably undergoes chemical reaction(s) through a process of Atomic Layer Deposition (ALD). Any compound and a combination of compounds suitable for use as a gaseous ALD precursor or a carrier, can be utilized.

The basics of an ALD growth mechanism are known to a skilled person. ALD is a special chemical deposition method based on the sequential introduction of at least two reactive precursor species to at least one substrate. It is to be understood, however, that one of these reactive precursors can be substituted by energy when using, for example, photon-enhanced ALD or plasma-assisted ALD, for example PEALD, leading to single precursor ALD processes. For example, deposition of a pure element, such as metal, requires only one precursor. Binary compounds, such as oxides can be created with one precursor chemical when the precursor chemical contains both of the elements of the binary material to be deposited. Thin films grown by ALD are dense, pinhole free and have uniform thickness. In some instances, Chemical Vapour Deposition (CVD) may be utilized.

The at least one substrate is typically exposed to temporally separated precursor pulses in a reaction vessel to deposit material on the substrate surfaces by sequential self-saturating surface reactions. In the context of this application, the term ALD comprises all applicable ALD based techniques and any equivalent or closely related technologies, such as, for example the following ALD sub-types: MLD (Molecular Layer Deposition), plasma-assisted ALD, for example PEALD (Plasma Enhanced Atomic Layer Deposition) and photon-enhanced Atomic Layer Deposition (known also as photo-ALD or flash enhanced ALD). The process can also be an etching process, one example of which being an ALE process.

A basic ALD deposition cycle consists of four sequential steps: pulse A, purge A, pulse B and purge B. Pulse A consists of a first precursor vapor (P1) and pulse B of another precursor vapor (P2). Inactive gas and a vacuum pump are typically used for purging gaseous reaction by-products and the residual reactant molecules from the reaction space during purge A and purge B. A deposition sequence comprises at least one deposition cycle. Deposition cycles are repeated until the deposition sequence has produced a thin film or coating of desired thickness. Deposition cycles can also be either simpler or more complex. For example, the cycles can include three or more reactant vapor pulses separated by purging steps, or certain purge steps can be omitted. On the other hand, photo-enhanced ALD has a variety of options, such as only one active precursor, with various options for purging. All these deposition cycles form a timed deposition sequence that is controlled by a logic unit or a microprocessor.

According to the method(s) disclosed hereby, the substrate material 10 to be coated undergoes, at first, a phase change from essentially liquid phase (such as water, for example) to essentially gaseous (vapour) phase, which results in generation of the gaseous species 101. Said species 101 react, in gaseous phase, with the precursor species (P1, P2). The latter are preferably sequentially delivered into the reaction space in the gaseous phase, to form essentially solid deposition layer(s) 121, 122 to produce a coating film 12.

The deposition process of the above mentioned layers 121, 122 involves formation of the particulate 11. The particulate 11 is formed, when the gaseous species 101 generated upon vaporizing of at least the portion of the substrate material 10 undergo chemical deposition reaction(s) with a chemical precursor or precursors, such as ALD precursor(s).

In some instances, the substrate 10 comprises a biodegradable material. Additionally or alternatively, the substrate 10 comprises at least one bioactive compound or an at least one pharmaceutically active compound provided in a suitable carrier. In some instances, the bioactive compound can be configured as the pharmaceutically active compound. In some other instances, the bioactive compound can be configured as biocide.

Figure 2:
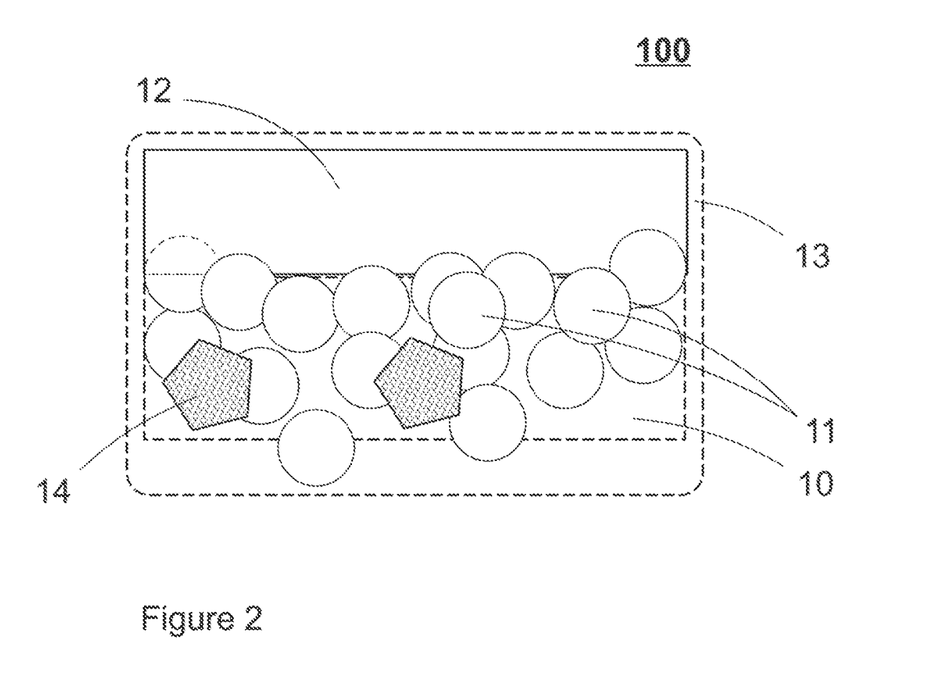

Mentioned bioactive compound(s) and/or pharmaceutically active compound(s) is/are designated on FIGS. 1 and 2 by reference numeral 14. The compound(s) 14 is/are embedded into the substrate 10 (which acts as the carrier material). It is preferred that mentioned compounds 14 do not evaporate/vaporize, but remain inside the substrate 10 until formation of the final product 100.

In certain configurations, the substrate material 10 is first allowed to absorb a predetermined reactant (e.g. water) so, that said reactant is then released to the gaseous phase (in the form of the species 101) to react with a predetermined precursor P1, P2 supplied in the gaseous phase, whereby particulate/powder will be generated on the substrate surface. In certain instances, the pulse of the precursor/reactant is not sufficiently separated (in time) to form a pure film for the duration of the porous film formation.

The substrate can thus be provided as a water-based hydrogel or sol-gel, which evaporates water. In some instances, the substrate can be liquid.

In some instances, a particulate substrate can be produced comprising particles 11 produced by the method described herein above. In said particulate substrate, the coating can comprise at least a metal compound.

During the coating process, a first stage is generation of particles 11 (2, FIG. 1), preferably, at least on the surface of the target material 10, 14. During subsequent steps (3, repeated), the deposition process can be a combination of the both precursors P1, P2, with at least some exposure to chemical substance(s) evaporating from the substrate, whereby the particles thus formed become coated layer-wise (see, 121, 122; step 4).

Optionally, a $3^{rd}$ phase can be applied (such as shown on FIG. 2), involving formation, by chemical deposition, of at least one additional coat 13 over the surface of the substrate 10 already coated with the film coating 12 to provide conformal encapsulation thereof. The additional coat 13 is a film deposited by a conventional gas phase deposition, such as ALD, which creates a conformal hole-free barrier.

The product 100 thus obtained can be provided as a partially coated/encapsulated substrate (FIG. 1, 4) or as a fully encapsulated substrate coated with an additional conformal film 13 (FIG. 2).

In this regard, a method for producing of at least partially encapsulated substrate 100 is further provided, said method comprising:
(i) obtaining a substrate (10);
(ii) vaporizing at least a portion of the substrate thus obtained, whereupon the substrate undergoes phase transition from essentially liquid phase to gaseous phase;
(iii) from the gaseous species (101) formed upon vaporizing at least the portion of the substrate material, producing particulate (11) that forms at least one coating layer (121, 122) on at least part of the surface of the substrate; and
(iv) from said at least one coating layer, formation of a film coating (12) at least partially encapsulating the substrate (10).

In some configurations, the method further comprises formation of an additional coat film 13 over the surface of the substrate 10 already coated, at least partly, with the film coating 12 deposited previously, to provide conformal, hole-free encapsulation thereof. Fully encapsulated structure 100 is thus created, as shown on FIG. 2.

At least density and/or porosity of the film coating 12, at least partially encapsulating the substrate, gradually change(s) in vertical direction, in accordance to what has been discussed herein above. For fully encapsulated substrates, without prejudice to an actual shape of the encapsulated substrate, vertical direction is defined in an essentially radial manner, i.e. from the center of the encapsulated product comprising the unreacted substrate 10 towards the topmost coating layer(s) of the coating film 12 and/or the additional coat 13.

Any one of said film coating 12 and the additional coat 13 can comprise at least one metal compound. Any one of the film coating 12 and the additional coat 13 can be deposited by conventional techniques based on the principles of chemical deposition in vapour phase, such as Chemical Vapour Deposition (CVD), Atomic Layer Deposition (ALD) or Plasma Enhanced Atomic Layer Deposition (PEALD).

Present disclosure further provides for formation of the product 100, which comprises partly or fully encapsulated substrate 10.

The product 100 comprises a substrate 10 and a film coating 12 deposited on at least a portion of a substrate material. The film coating 12 comprises at least one coating layer. At least density and/or porosity of the film coating 12 gradually change(s) in vertical direction, in accordance to what has been discussed hereinabove.

In the product 100, the at least partially encapsulated substrate 10 is provided in the form of any one of liquid, gel, hydrogel or sol-gel. Any other colloid system, such as emulsion, for example, may be utilized.

The product can be further deposited with the additional coat 13 formed over the surface of the substrate 10 already coated, at least partly, with the film coating 12, to provide conformal encapsulation thereof.

The product is advantageously produced by any one of the methods described herein above.

Based on the product 100, a bioactive composition and/or a pharmaceutical preparation configured for gradual release can be prepared. The bioactive composition may be rendered with at least one biological activity including but not limited to anti-inflammatory-, antibacterial-, biocidal- and fungicidal activities, and the like. In some instances, the bioactive composition may be configured as the pharmaceutical preparation, i.e. as a preparation configured to exert at least one therapeutic effect onto a human or a non-human mammal. An exemplary pharmaceutical preparation provided with a conformal encapsulation 13 is schematically illustrated on FIG. 2.

Application areas of the process described hereby include, but are not limited to:
capping of hydrogel or sol-gel with a moisture tight gas barrier;
manufacturing a medicine/a pharmaceutical preparation, configured to dissolve gradually, whereby gradually increasing medicine gradient over dissolving time of the chemically deposited film coating (12, 13).

In latter case, when the medicine (e.g. a pill) is administered to a patient, the coating 12, 13, manufactured according to the method(s) described hereby dissolved gradually, whereby at first the rate of medicine release is smaller/slower (upon dissolution of the conformal film 13, FIG. 2), which rate increases over time (upon dissolution of the particulate-created coating 12; step 4, FIG. 1).

The product 100 comprising the deposited material, such as medicine 14, provided in the substrate carrier 10, can also be removed from the substrate holder 21 configured as a medicine container (4, FIG. 1), so that exposure of the patient to the medicine at the substrate side starts first. It should be noted that concentration of the bioactive- and/or pharmaceutical compounds 14 increases in direction towards the unreacted substrate 10 (in where said compounds 14 are provided in the substrate carrier material).

Hence, in view of a route of administration of a drug—some routes are more aggressive to certain drugs. For example, orally administered drug is exposed to such competing substances as acids, alkali and many other substances. The film coating 12, optionally together with the additional coat 13, produced by the method(s) disclosed hereby can control with high precision time (time point), where the drug should be absorbed.

Further, the coating film 12, 13 can be used to modulate a release rate of the drug (constant, accelerated, slowed down) and/or to establish drug release with prominent phases (e.g. initially constant or accelerated or slowed down (phase I); followed by another phase, different from the previous one (Phase II), etc.). Additionally, the film coating 12, optionally together with 13, can be configured to contain- and release different drugs at different time points.

The structure 100 can further implemented as a multilayer, complex stack structure, wherein the first substrate 10 comprising a first bioactive compound (e.g. a first medicine) and coated with the film coating 12 and optionally with the additional coat 13 can be further applied with a second substrate 10 (not shown) comprising a second bioactive compound (e.g. a second medicine) by dipping into a solution comprising said medicine, for example. Thereafter, the entire structure can undergo deposition of the second coating film 12 (not shown) optionally covered by the conformal coat 13. The procedure can be repeated several times such, that in the resulting multilayer structure each individual "sub-layer" (10, 12 and optionally 13) comprises the same drug or different drugs configured for sequential release.

Thus, the medicine the patient is in need of is efficiently delivered to the body. Such method of administration is highly sustainable (very small amounts of drug are wasted, due to efficient delivery (bioavailability); and a number of side effects is markedly reduced.

In some other instances, the bioactive compound can be configured as biocide. Examples of biocides include, but are not limited to the substances with antibacterial and antimicrobial properties (such as wound care, for example), disinfectants for skin, and the like.

The invention further concerns a device for coating a vaporizing substrate. The device (not shown) is configured to deposit the film coating 12 comprising at least one coating layer onto at least a portion of a substrate material that undergoes phase transition from essentially liquid phase to gaseous phase, wherein said substrate comprises a chemical substance that participates in chemical deposition reaction(s) in gaseous phase.

The device is a reactor apparatus preferably configured to exploit principles of vapor-deposition based techniques. In terms of an overall implementation, the reactor may be based on an ALD installation described in the U.S. Pat. No. 8,211,235 (Lindfors), for example, or on the installation trademarked as Picosun R-200 Advanced ALD system available from Picosun Oy, Finland. Nevertheless, the features underlying a concept of the present invention can be incorporated into any other chemical deposition reactor embodied as an ALD, PEALD, MLD (Molecular Layer Deposition) or CVD device, for example.

The reactor comprises the reaction chamber that establishes the reaction space (deposition space), in which the method(s) described hereinabove take place. The reactor further comprises a number of appliances configured to mediate fluidic flow (inert fluids and reactive fluids containing precursor compounds P1, P2) into the reaction chamber. Mentioned appliances are provided as a number of intake lines/feedline and associated switching and/or regulating devices, such as valves, for example.

Precursor(s) P1, P2 are delivered into the reaction space in an essentially gaseous form. Reactive fluid entering the reaction chamber through at least one feedline is preferably a gaseous substance comprising a predetermined precursor chemical carried by an inert carrier (gas). Delivery of the precursor chemicals into the reaction space and film growth on the substrate is/are regulated by means of the abovesaid regulating appliances, such as e.g. three-way ALD valves, mass-flow controllers or any other device suitable for this purpose.

The device further comprises an evacuation line for discharging an exhaust flow out of the reaction chamber. The evacuation line constitutes a fore-line for an evacuation pump and it may comprise, in some configurations, a closing valve, preferably upstream the pump unit. It is preferred that withdrawal of fluidic substance from the reaction chamber is implemented in an uninterrupted manner, whereby the pump, preferably configured as a vacuum pump, removes fluidic substance from the reaction chamber continuously during the entire deposition process.

It shall be appreciated by those skilled in the art that the embodiments set forth in the present disclosure may be adapted and combined as desired. The disclosure is thus intended to encompass any possible modifications of the device and the deposition method, recognizable by those of ordinary skill in the art, within a scope of appended claims.

The invention claimed is:

1. A method for coating a vaporizing substrate, wherein a film coating comprising at least one coating layer is deposited, during a process of vaporization of the substrate, on at least a portion of a substrate material that undergoes phase transition from essentially liquid phase to gaseous phase, and wherein the substrate comprises a chemical substance that participates in chemical deposition reaction(s) in gaseous phase.

2. The method of claim 1, wherein the film coating is deposited onto the substrate material being vaporized from at least a surface of the substrate.

3. The method of claim 1, in which gaseous species are formed upon vaporizing at least the portion of the substrate material, wherein said gaseous species, when undergoing chemical deposition reactions in gaseous phase, produce particulate that forms at least one coating layer on at least part of a surface of the substrate.

4. The method of claim 1, wherein said at least one coating layer comprises a metal compound.

5. The method of claim 1, wherein at least density and/or porosity of the film coating gradually change(s) in vertical direction.

6. The method of claim 1, wherein the vaporizing substrate is a liquid substrate.

7. The method of claim 1, wherein the vaporizing substrate is a colloid substrate.

8. The method of claim 7, wherein the vaporizing substrate is gel, hydrogel or sol-gel.

9. The method of claim 1, wherein the vaporizing substrate undergoes chemical reaction(s) through a process of chemical deposition in vapour phase, wherein the process of chemical deposition in vapour phase is Chemical Vapour Deposition or Atomic Layer Deposition.

10. The method of claim 1, in which particulate is formed, when gaseous species formed upon vaporizing of at least the portion of the substrate material undergo chemical deposition reaction(s) with a chemical precursor or precursors.

11. The method of claim 10, wherein the chemical precursor or precursors are ALD precursor(s).

12. The method of claim 1, wherein the substrate comprises a biodegradable material.

13. The method of claim 1, wherein the substrate comprises at least one of a bioactive compound, a pharmaceutically active compound or a combination thereof.

14. The method of claim 1, further comprising formation of at least one additional coat over a surface of the substrate already coated with the film coating to provide conformal encapsulation thereof, wherein said additional coat is deposited by a process of chemical deposition in vapour phase, wherein the process of chemical deposition in vapour phase is Chemical Vapour Deposition or Atomic Layer Deposition.

15. A method for producing of at least partially encapsulated substrate, comprising:
  (i) obtaining a substrate;
  (ii) vaporizing at least a portion of the substrate thus obtained, whereupon the substrate undergoes phase transition from essentially liquid phase to gaseous phase;
  (iii) during the step (ii) vaporization of the substrate, from the gaseous species formed upon vaporizing at least the portion of the substrate material, producing particulate to form at least one coating layer on at least part of a surface of the substrate; and
  (iv) during the step (ii) vaporization of the substrate and from said at least one coating layer, formation of a film coating at least partially encapsulating the substrate.

16. The method of claim 15, further comprising formation of an additional coat over the surface of the substrate already coated with the film coating, to provide conformal encapsulation thereof.

17. The method of claim 15, wherein at least density and/or porosity of the film coating gradually change(s) in vertical direction.

18. The method of claim 15, wherein any one of the film coating and the additional coat comprises a metal compound.

19. The method of claim 15, wherein any one of the film coating and the additional coat is/are deposited by a process of chemical deposition in vapour phase, wherein the process of chemical deposition in vapour phase is Chemical Vapour Deposition or Atomic Layer Deposition.

\* \* \* \* \*